United States Patent
Frost et al.

(10) Patent No.: US 7,201,060 B2
(45) Date of Patent: Apr. 10, 2007

(54) **APPARATUS AND METHOD FOR DETERMINING *IN SITU* PORE FLUID AND SOIL PROPERTIES USING MULTI-SENSOR MEASUREMENT SYSTEMS**

(75) Inventors: James David Frost, Atlanta, GA (US); Jason Theodore DeJong, Davis, CA (US); Gregory L. Hebeler, Atlanta, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 210 days.

(21) Appl. No.: 10/693,624

(22) Filed: Oct. 24, 2003

(65) Prior Publication Data

US 2004/0118199 A1    Jun. 24, 2004

Related U.S. Application Data

(63) Continuation-in-part of application No. 09/907,412, filed on Jul. 17, 2001, now Pat. No. 6,701,771.

(60) Provisional application No. 60/218,817, filed on Jul. 18, 2000.

(51) Int. Cl.
*G01L 11/00* (2006.01)

(52) U.S. Cl. .......................... 73/784; 73/9

(58) Field of Classification Search ............... 73/38, 73/84, 784, 9
See application file for complete search history.

(56) References Cited

U.S. PATENT DOCUMENTS

| | | | | |
|---|---|---|---|---|
| 4,453,401 A | * | 6/1984 | Sidey | 73/73 |
| 5,319,959 A | * | 6/1994 | Cooper et al. | 73/84 |
| 5,921,328 A | * | 7/1999 | Babineau et al. | 175/20 |
| 6,208,940 B1 | * | 3/2001 | Kram et al. | 702/12 |

OTHER PUBLICATIONS

Definitions of "sleeve" and "mandrel" from American Heritage Dictionary, 1982.*

* cited by examiner

*Primary Examiner*—Robert Raevis
(74) *Attorney, Agent, or Firm*—Thomas, Kayden, Horstemeyer & Risley, LLP

(57) ABSTRACT

An apparatus and methods for determining in situ pore fluid and soil properties at a particular subsurface location are disclosed. In one embodiment, the apparatus comprises a penetrating tip member configured to penetrate soil. The apparatus further comprises an attachment module coupled to the penetrating tip member. The attachment module includes at least one mandrel that includes a piezo sensor. An in situ measurement of pore pressure is obtained by the piezo sensor at a depth that corresponds to the location of the at least one mandrel on the attachment module.

24 Claims, 12 Drawing Sheets

(a)

(b)

(c)

(d)

APPARATUS AND METHOD FOR DETERMINING *IN SITU* PORE FLUID AND SOIL PROPERTIES USING MULTI-SENSOR MEASUREMENT SYSTEMS

CROSS-REFERENCE TO RELATED APPLICATION

This application is a continuation-in-part of U.S. application Ser. No. 09/907,412 filed, Jul. 17, 2006, now U.S. Pat. No. 6,701,771, issued Mar. 9, 2004, entitled "Multi-Friction Sleeve Cone Penetrometer Apparatus and Method," and also claims the benefit of U.S. provisional application, Ser. No. 60/218,817, filed Jul. 18, 2000, which are entirely incorporated herein by reference.

TECHNICAL FIELD

The present disclosure is generally related to geotechnical systems and geotechnical structure elements and, more particularly, an apparatus and method for in situ measurement of the relationship between interface strength and surface roughness of materials for the purpose of establishing friction parameters and characteristics. The present disclosure is further related to an apparatus and method for determining pore fluid and soil response in situ at a particular subsurface location as a result of penetration of a multi-sensor device.

BACKGROUND OF THE INVENTION

In geotechnical engineering, one factor, among others, for consideration when designing geotechnical systems is the particulate-continuum interface. This interface occurs between the soil and the geotechnical structural members (e.g. soil-concrete, soil-steel, and soil-geomembrane). Although a significant amount of research has been performed on the behavior of soil masses under typical loading and straining conditions in geotechnical systems, the region where the geotechnical structural members and soil masses come into contact—the soil-geomaterial interface—has received markedly less attention.

The interface is a factor, among others, governing the performance of many geotechnical systems, including for example deep foundations, micro-tunneling, liner systems (e.g. landfills, canal liners, and leach ponds), and an assortment of retaining structures such as anchored, reinforced, and soil nailed walls. The importance of the characteristics and behavior of the interface between man-made geomaterials and soils in the overall system performance varies from application to application, but is usually reflected in some manner in the design methodology and associated calculations for each geotechnical system. Because the structural integrity of many systems is dependant upon accurate calculations and designs for the soil-geomaterial interface, correctly measuring the performance characteristics of the interface is crucial.

Another factor for consideration when designing geotechnical systems is the pressure of the fluid phase of permeable soils and sediment, which is called the pore fluid pressure. The measurement of pore fluid pressure can facilitate the identification of the groundwater table elevation, as well as the strength, compressibility, and permeability of the soil.

There are many different types of penetrating probes for detecting and measuring soil properties and characteristics or for detecting and measuring the properties and characteristics of underground substances, such as water, gases, contaminants, etc. Probes that test for underground substances are often used primarily in association with environmental applications. For instance, U.S. Pat. Nos. 6,208,940 and 6,236,941 both to Kram appear to describe a piezocone having a conical tip attached to the lower end of a smooth friction sleeve, where the sleeve measures the resistance of the soil. The Kram inventions use the piezocone to develop hydrostatic and hydraulic plots for detecting the depth of subsurface water and groundwater contamination.

In U.S. Pat. No. 5,663,649 to Topp, a soil penetrometer and method are disclosed which are capable of determining the soil moisture content via in situ measurements and simplified calculations. The penetrometer appears to have a releasably engageable tip and utilizes an electromagnetic field to detect moisture. Other prior art utilizes a variety of techniques in combination with penetrometers to detect and measure in situ characteristics, such as chemical composition for identification of contamination. For instance, U.S. Pat. No. 6,097,785 to Elam appears to disclose the use of a penetrometer equipped with x-ray fluorescence spectroscopy to identify hazardous waste; U.S. Pat. No. 6,147,754 to Theriault appears to use laser induced breakdown spectroscopy in conjunction with a penetrometer to identify soil contamination; U.S. Pat. No. 6,018,389 to Kyle appears to use fiber optic raman spectroscopy probes to provide in situ chemical analysis; and U.S. Pat. No. 5,497,091 to Bratton appears to teach the use of cone penetration testing (CPT) in conjunction with a surface-mounted pH sensor to provide continuous pH profiling with depth during penetration.

It is also known in subsurface testing systems to utilize cone and sleeve strain sensors to detect certain soil characteristics. In U.S. Pat. No. 5,635,710 to Reed, a detachable sleeve is apparently used to provide strength and protection to the radiation sensor probes which detect subsurface formations, and U.S. Pat. No. 5,902,939 to Ballard appears to disclose a penetrometer having cone and sleeve strain sensors used to calculate soil classifications and soil layers in "real-time" during penetration. Likewise, in U.S. Pat. No. 5,726,349 to Palmertree, a system and method for determining the shear resistance of soil with a portable and partially automated cone penetrometer is provided, where the field data outputs are stored and then transferred to a computer for tabulating.

SUMMARY OF THE INVENTION

The present disclosure is related to apparatus and methods for determining pore fluid and soil response in situ at a particular subsurface location. In one embodiment, the apparatus for determining interface strength in situ at a particular subsurface location comprises an attachment module that includes a plurality of individual load cells. The plurality of load cells can be configured in series, each of which measures the interface resistance due to the penetration of a sleeve with a selected surface texture into the soil. This configuration provides for multiple individual in situ measurements of interface strength at each measurement depth in a single sounding. The sleeves are interchangeable so that measurements corresponding to any desired roughness can be determined. In addition, with multiple friction sleeve measurement $f_s$ values recorded at any given elevation within the same sounding, factors that affect $f_s$ can easily be determined since the lateral variability of the site is not an issue in the measurements.

In a preferred embodiment, the attachment module is configured with four individual load cells, each having a mandrel and a friction sleeve. Thus, the four load cells correspond to four multi-friction sleeve module measurements of interface strength. Additionally, in a preferred embodiment, the attachment module is configured with a conventional 15 cm² CPT, allowing for simultaneous measurements of conventional CPT sensors (e.g., $q_c$, $u_2$, and $f_s$) in addition to the four multi-friction sleeve module measurements. Thus, the combined CPT module-attachment module system can provide seven individual in situ measurements of interface strength at each measurement depth in a single sounding.

In another embodiment, non-instrumented tips of varying lengths can be used with the penetrometer attachment in place of a conventional CPT module. Regardless of the specific configuration utilized, it is anticipated that the penetrometer attachment will enable direct in situ measurement of the relationship between surface roughness, hardness and interface strength.

In another embodiment, an apparatus for determining in situ pore fluid and soil properties at a particular subsurface location comprises a penetrating tip member configured to penetrate into the soil of the subsurface location. The apparatus further comprises an attachment module coupled to the penetrating tip member. The attachment module includes at least one mandrel that includes a piezo sensor. An in situ measurement of pore pressure is obtained by the piezo sensor at each measurement depth that corresponds to the location of each mandrel on the attachment module. Each piezo sensor individually measures in situ the pore fluid pressure at its corresponding measurement depth.

In a preferred embodiment, the attachment module comprises a plurality of individual load cells, wherein at least one load cell is coupled adjacent to at least one piezo sensor. Each load cell has a friction sleeve with a surface texture of a particular smoothness and/or roughness. Each piezo sensor is isolated to sense the pore fluid pressure at its corresponding measurement depth. Each piezo sensor measures the pore fluid pressure induced by each friction sleeve of the individual load cells. Each piezo sensor has a value at a measurement depth for each friction sleeve of the individual load cells in a single sounding, with those values corresponding to the individual in situ measurements of pore fluid pressure at the measurement depth for each load cell.

These embodiments provide a method for determining in situ soil properties. In particular, a method is disclosed for direct, in situ measurement of the interface strength throughout the soil profile depth by determining the relationship between the interface strength and the hardness and surface roughness factors at desired measurement depths in a single sounding. In this regard, one embodiment of such a method, among others, can be broadly summarized by the following steps: collecting penetrating tip measurements; collecting attachment module measurements for each of the plurality of individual load cells, where the load cells are comprised of a corresponding plurality of friction sleeves; and transmitting the measurement data to a data acquisition system for manipulation and storage. This method may also include the steps of monitoring verticality, converting analog data to digital data, multiplexing data signals downhole, arranging a plurality of load cells in series, and configuring the attachment module for rapid set-up and easy modifications and configuring the friction sleeves with a diamond textured sleeve surface that is "self-cleaning" and capable of inducing shearing within the soil, instead of just along the interface.

In another embodiment, a method of determining in situ soil properties comprises positioning a penetrating tip member so as to penetrate into the soil at a particular subsurface location. An attachment module is positioned in a predetermined relationship to the penetrating tip member so as to form a penetrometer comprised of at least the penetrating tip member and the attachment module. The penetrating tip member end of the penetrometer is forced into the soil and preferably, allows measurements to be collected from the penetrating tip member. Measurements from the attachment module are collected from at least one piezo sensor located in the attachment module. The attachment module comprises at least one mandrel, wherein at least one mandrel comprises a piezo sensor that obtains an in situ measurement of pore fluid pressure at each measurement depth that corresponds to the location of each mandrel on the attachment module.

Other systems, methods, and features of the apparatus and methods will be or will become apparent to one with skill in the art upon examination of the following drawings and detailed description. All such additional systems, methods, and features are included within the scope of the present apparatus and methods, and protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present apparatus and methods. Moreover, in the drawings, like reference numerals designate corresponding parts throughout the several views.

DETAILED DESCRIPTION

Figure 1:
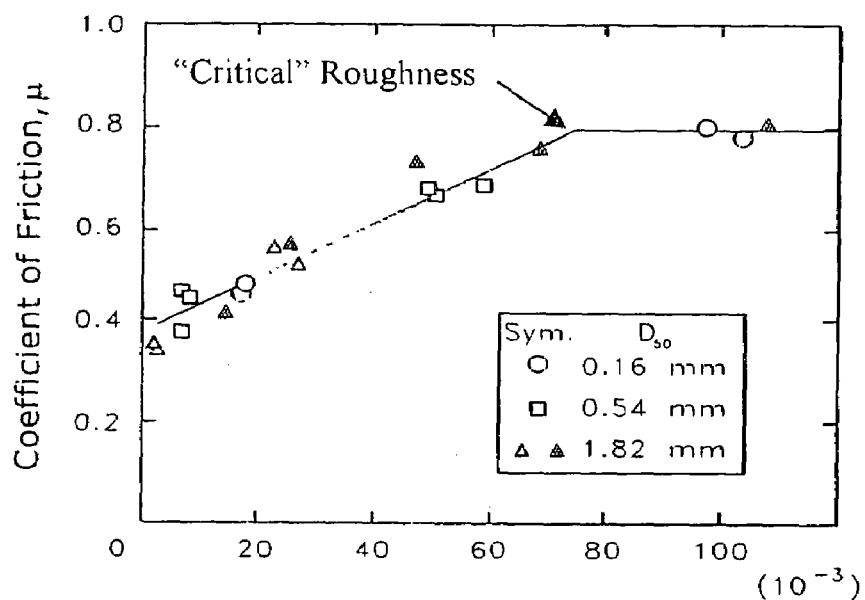
FIG. 1 is a graphical representation of the bilinear relationship between surface roughness and a friction coefficient (Prior Art).

Disclosed are systems and methods for direct in situ measurement of pore fluid and soil response, particularly interface strength and pore fluid pressure. The systems and methods can eliminate the need for a number of critical empirical adjustment factors currently required in the estimation of interface strength and can further measure the pore fluid pressure to better understand the characteristics and nature of the soil.

Through recent advances in the study of particulate-continuum interfaces, two factors have been identified which are considered instrumental in identifying the behavior of the interfaces, namely the surface roughness and hardness. First, the continuum surface roughness should be quantified kinematically in a dimensionless manner in relation to the size of the contacting particulate media. This is accomplished by quantifying the effective roughness experienced by contacting particles. Second, the hardness of the surfaces must be quantified using established hardness tests. While each of these factors has been known for some time, the importance of their coupled effect on interface strength had not been uncovered.

In many cases, the behavior of the interface is currently estimated by applying a series of adjustment factors to estimated properties of the soil mass. In other cases, the soil-geomaterial interface strength is determined through interface shear tests performed in the laboratory and then corrected by adjustment factors. Both of these approaches are empirical and depend on appropriate engineering judgment regarding numerous characteristics including subsurface variability, soil type and density, strain rate, surface roughness and state of stress among others.

A number of factors are known to affect, in varying degrees, the soil-geomaterial interface behavior. See Table 1 below.

TABLE 1

Factors Affecting Soil-Geomaterial Interfaces

| Type | Factor | Significance |
|---|---|---|
| Soil | Angularity | High |
|  | Density | High |
|  | Initial Soil Structure | Low |
|  | Mean Grain Size ($D_{50}$) | Medium |
|  | Surface Roughness | Low |
|  | Uniformity Coefficient ($C_u$) | Low |
| Geomaterial | Surface Hardness | High |
|  | Surface Roughness | High |
| Testing | Normal Stress | High |
|  | Test Method | Low |
|  | Strain Rate | High |

Factors that generally have a lesser effect on the strength of such interfaces include the test method and the soil properties, including initial soil structure and coefficient of uniformity. Other factors, including the normal load, strain rate, particle angularity, mean particle size ($D_{50}$), and the geomaterial hardness and surface roughness may have a significant effect on both the peak and residual interface strength. In particular, the surface roughness and the hardness factors are known to be influential on the interface strength.

Surface roughness, in particular, has been identified as having a significant impact on interface strength. The interface strength increases with surface roughness to a limiting value until it becomes equal to the internal strength of the soil, at which stage shearing is transferred from the interface into the soil. Automated profiling devices are now able to readily quantify the surface characteristics, which has led to the proposal of a large number of international surface roughness standards. The most universally accepted parameter for quantifying surface topography is the average roughness, $R_a$, defined as:

$$R_a = \frac{1}{L}\int_0^L |z| dx \quad (1)$$

where L is the sample length and z is the absolute height of the profile from a mean line. Unfortunately, $R_a$ may not distinguish between a relatively gently undulating surface and those with a more undulating profile. This limitation can result in surfaces that induce different mechanisms during interface shearing having similar $R_a$ values. Not withstanding this limitation, it is noted that $R_a$ is typically used to describe surface roughness.

Quantification of the role of geomaterial surface roughness on interface strength has necessitated a normalizing of the surface roughness to the average particle size of the contacting soil. The normalized roughness parameter, $R_n$, defined as:

$$R_n = \frac{R_{max}(L = D_{50})}{D_{50}} \quad (2)$$

where $R_{max}$ is the absolute vertical distance between the highest peak and the lowest valley along the surface profile over a sample length equal to $D_{50}$, the average particle diameter. Using $R_n$, the relationship between surface roughness and interface friction was found to be bilinear (see FIG. 1-Prior Art). Along the left-hand portion of the curve, below a certain "critical" roughness, the interface strength increases in a linear fashion proportional to the increase in surface roughness with particles primarily sliding along the surface. At the "critical" surface roughness, shearing transfers from the interface into the adjacent soil body when the interface friction becomes equal to the internal friction angle, or internal frictional strength of the contacting soil, since the normal stress is known. The right-hand portion of the curve reflects an essentially constant coefficient of friction, or internal frictional strength, thus indicating that additional increases in surface roughness above the "critical" surface roughness have no added effect.

Measurement of the particle movements near the interface during interface shear tests is known to show that little particle movement is observed at the interface below peak stresses. Conversely, after peak, the primary mechanism of interface movement is slippage of the soil particles along smooth surfaces, and slipping, rolling, and vertical displacement for rough surfaces while translating along the interface. This behavior is further known to affect an increasing zone of particles as the surface roughness increases. For instance, in smooth surfaces, the particles sliding along the interface dominate the behavior, with minor variations in density being limited to a zone one to two particle diameters thick adjacent to the surface. As the surface roughness increases, the size of the affected zone increases to a distance of about five or six particle diameters from the interface. Thus, the bilinear relationship between the surface roughness and the interface behavior is known to be consistent.

Figure 2:
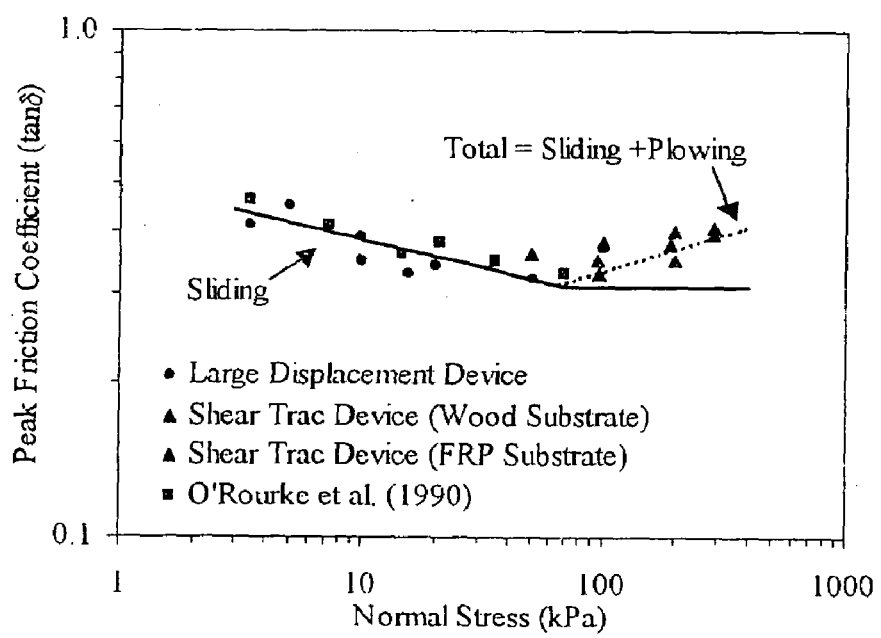
FIG. 2 is a graphical representation of the relationship between particle stress and the friction coefficient (Prior Art).

The other factor known to have significant impact on the interface behavior is the surface hardness. In tribology, the hardness of the materials present at the interface, in combination with other factors, has been identified to determine the type of surficial wear (e.g. abrasive versus adhesive), the size of the actual contact areas, and the type of contact deformation (e.g. elastic versus plastic) among others. This understanding in tribology has recently been extended to soil-geomaterial interfaces to show that for a given geomaterial hardness, the interface friction will initially decrease as the normal force, and hence, global stress increases. (See FIG. 2-Prior Art).

This effect is known to occur because as the normal force increases, the number and area of particles contacting the surface increases, thus causing the actual contact stress per particle to decrease and therefore the interface friction to decrease. At a critical stress, the number and size of individual contacts per unit area reaches a maximum value, causing any additional increase in normal force and hence global stress to be directly transmitted to each particle-surface contact. The mechanism of particle movement at the interface is thus directly related to the magnitude of normal force (or global stress) relative to the hardness of the surface material. At global stresses less than the critical stress, the stress at each particle contact is less than what is required to damage a surface of a given hardness. When this occurs, sliding without damage to the surface is the primary mode of translation. However, when the stresses at particle contacts are greater than the critical stress, particle motion along the surface involves both sliding and plowing.

Plowing occurs when the stresses at the interface exceed what is required to damage the surface, forcing particles to penetrate the surface and remove or displace material from the surface during translation. When plowing occurs in addition to sliding, the force required to displace the soil relative to the surface increases, resulting in an increase in interface friction. The critical stress is dependent on the particulate angularity with the critical stress increasing with decreasing angularity. Furthermore, wearing is more evident at low hardness, while high hardness discourages abrasive wear and changes in surface roughness.

With increasing frequency, the CPT is the device of choice used to obtain in situ measurements of interface strength. The three primary measurements of the CPT are $q_c$, $u_2$ and $f_s$. Factors that have been considered to effect $q_c$ measurements include temperature, the apex angle of the penetrating tip, the wear of the penetrating tip, the penetration rate, and the pore pressure acting on the back of the penetrating tip among others. With the more recent piezocone designs, a portion of the back of the penetrating tip element is exposed, requiring the $q_c$ measurement to be converted to the corrected cone tip resistance, $q_1$ to account for the effect of pore pressure acting on the back of the tip element.

Similarly, the $u_2$ measurement is adversely affected by the degree of saturation of the soil being penetrated and/or that of the porous element, the pore pressure element location, the axial load, and the horizontal stress. For example, incomplete saturation of the porous element may result in a compressible fluid-air mixture that decreases measurement resolution. In addition, the location of the pore pressure element has a significant effect on the measured value. In most soils, the pore pressure rapidly increases at the tip, reaching a maximum value at the shoulder of the CPT, and then decreases until it reaches a stable value. Accordingly, most standard CPT module designs isolate the pore pressure measurement from the $q_c$ measurement, thereby eliminating any interaction.

The friction sleeve measurement $f_s$ involves several factors that affect its measurement accuracy. These factors include load cell arrangement, sleeve surface roughness, sleeve wear, sleeve length, sleeve location and module stiffness.

Load cells are typically arranged in one of two manners—subtraction cone load cell arrangement, where $f_s$ is determined by calculating the difference between the tip and total (sleeve plus tip) load, or isolated load cell arrangement, where the tip and sleeve resistances are measured separately. Of these two designs, the subtraction type load cell arrangements are more common than individual load cell arrangements due to their greater durability and ease of design and manufacturing. However, individual load cell designs can lead to significantly improved resolution of the $f_s$ measurement since $f_s$ is typically more than one order of magnitude less than $q_c$ and, thus, a load cell with a smaller range can be used for the $f_s$ measurements. Since the resolution is a function of the full-scale capacity, a load cell with a smaller range has a higher absolute resolution. ASTM D5778 (1995) estimates that the standard deviation of the $f_s$ measurement for subtraction type designs and individual load cell designs to be 15% and 5% of the full-scale load cell output, respectively. The importance of the CPT load cell arrangement has long been recognized and isolated load cell arrangements are now being incorporated into new penetrometer designs.

ASTM D3441 (1994) and ISSMFE (1989) standards for CPTs specify that the friction sleeve roughness, $R_a$ (average roughness), must be equal to 0.50±0.25 μm. In application, surface roughness measurements may vary greatly, from the time of shipment by the manufacturer, and throughout the service life of the sleeve. The surface roughness may change irregularly with each sounding, decreasing or increasing depending on the soil type encountered and indicative of continuous sleeve wear. Large variations in surface roughness measurements are undesirable, particularly given that a small change in surface roughness can have a large impact on the interface strength of relatively smooth surfaces.

After repeated use, the cone tip and friction sleeve experience significant wear, decreasing in tip and sleeve diameters, respectfully. Usually, the diameter of the sleeve decreases inconsistently along its length, with the top portion wearing more. This uneven wear results in improper contact between the friction sleeve and the soil and may cause as much as a 50% decrease in the $f_s$ measurement. Recognizing the effect of wear, guidelines have also been put forth relative to the control of the effect of CPT tip and friction sleeve wear through national (ASTM D5778 1995) and international (ISSMFE 1989) standards. These standards specify that the friction sleeve diameter should always be equal to or up to 0.35 mm larger in diameter than the cone tip. Prompt replacement of the worn components can maintain the error due to wear below about 5%.

The effect of sleeve length on the $f_s$ measurement is also known to be important. Specifically, the sleeve length adversely affects soil classification, layer detection, and anomaly detection to varying degrees, depending on the statistical properties (i.e. mean, variance, fluctuation distance) of the stratigraphy in a given sounding.

Many researchers have shown that the position of the friction sleeve relative to the CPT tip significantly affects the friction sleeve measurement. Variation in $f_s$ is thought to be primarily due to the variation in horizontal stress acting along a CPT—the "baseline" horizontal stress equal to the natural in situ lateral stress prior to penetration and the variation from the "baseline" stress due to insertion of the CPT. This apparent variation in horizontal stress primarily occurs in a rapidly changing stress zone beginning around the CPT tip and extending up a portion of the CPT shaft. Consequently, $f_s$ measurements outside of the highly variable stress zone are preferable and may be accomplished by positioning the friction sleeve further up the CPT shaft instead of directly behind the CPT tip. Unfortunately, most current designs position the friction sleeve directly behind the tip in accordance with national standards (ASTM D5778 1995).

The module stiffness, of a standard CPT as opposed to a stiff CPT, is known to adversely affect the $f_s$ measurement. "Bending" of the CPT may introduce additional irregularity into the conventional friction sleeve measurement due to "shadowing" of a portion of the sleeve by the tip. While this effect can be minimized by using a full eight gauge bridge transducer and increasing the device stiffness to minimize bending, not all penetrometers incorporate these design considerations.

Variations in any of the foregoing factors can significantly affect the measurements obtained during in situ penetration testing and lead to inaccurate data.

Figure 3:
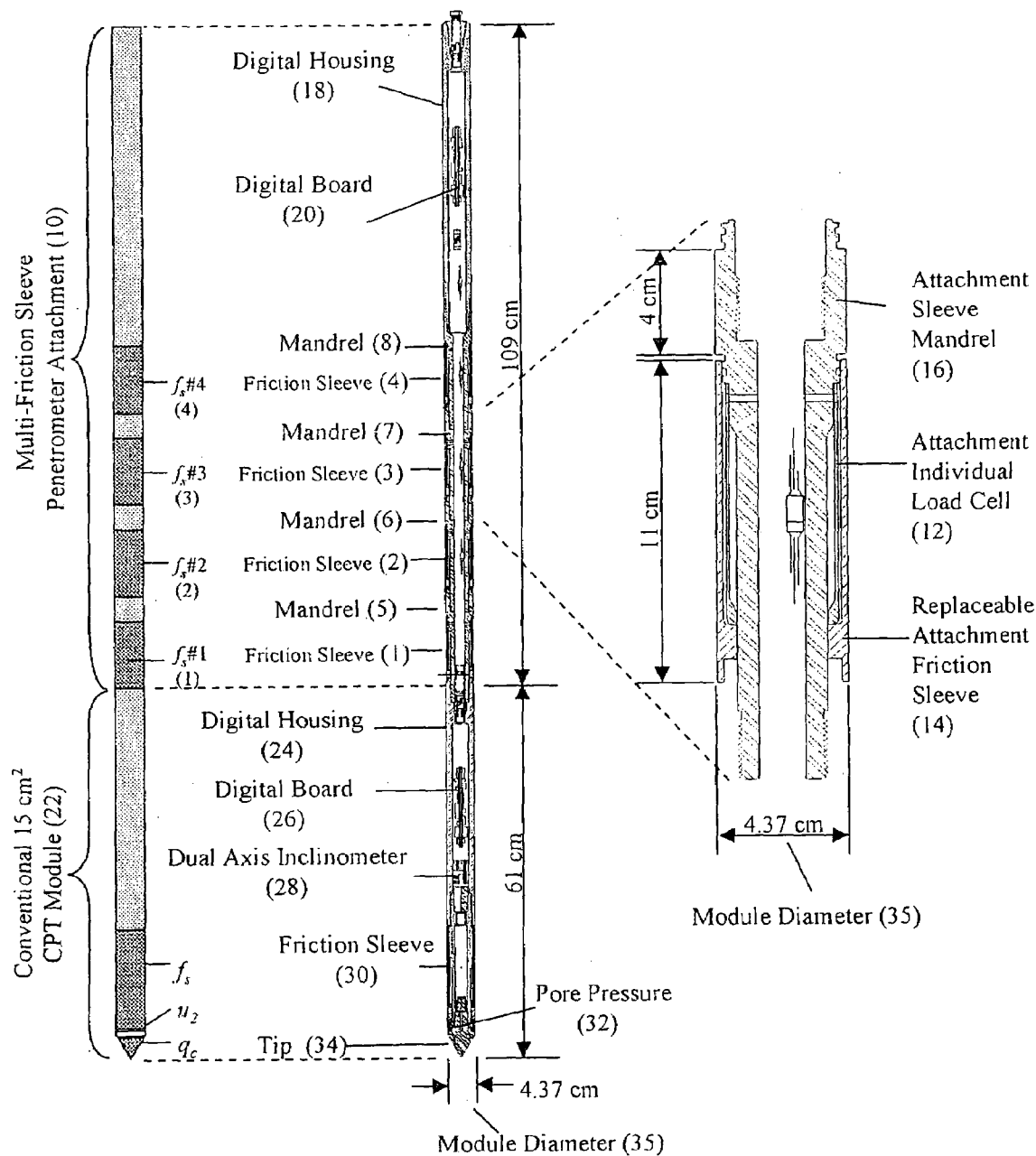
FIG. 3 is a schematic diagram showing an embodiment of the multi-friction sleeve attachment module configured with a conventional CPT module.

As shown in FIG. 3, in a preferred embodiment the multi-friction sleeve penetrometer attachment module (attachment module) 10 is equipped with four individual load cells 12 (i.e. combination of friction sleeve 14 and sleeve mandrel 16) in series, each of which measures the interface resistance due to the penetration of a sleeve 14 with a selected surface texture into the soil. The friction sleeves are vertically arranged in ascending order according to increasing roughness of surface texture. In this manner, the friction sleeve with the least rough surface texture is placed closest to the end of the attachment module that will be coupled to a penetrating tip member, while the friction sleeve with the roughest surface texture is placed at the end of the attachment module that will be furthest away from the penetrating tip member. This configuration provides four individual in situ measurements of interface strength at each measurement depth (e.g., the depths which correspond to the location of each of the friction sleeves) in a single sounding. The load cells 12, digital housing 18 and digital board 20 comprise the attachment module 10, which, in a preferred embodiment, may be attached to a conventional CPT module 22. With the sleeves 14 being interchangeable, sleeves 14 of any desired roughness can be used in a given sounding. In addition, with multiple $f_s$ values being recorded at any given elevation within the same sounding, factors that affect $f_s$ can easily be determined since lateral variability at the site is not an issue. Furthermore, configuration with a conventional CPT module 22 permits simultaneous measurements of conventional CPT sensors (e.g. $q_c$, $f_s$, and $u_2$) in addition to the multi-sleeve attachment measurements. Typically, a CPT module 22 comprises a digital housing 24, a digital board 26, a dual axis inclinometer 28, a friction sleeve 30, a pore pressure tip 32, and a cone tip 34. When used with the CPT 22, the total instrument length is approximately 170 cm, with the attachment module 10 being approximately 109 cm in length including the digital housing 18, and the conventional CPT module 22 being approximately 61 cm in length. (See Table 2 below). It should be noted, however, that non-instrumented tips of varying lengths may be used with the attachment module 10 in place of the conventional CPT module 22.

TABLE 2

Summary of Specifications for a Preferred Embodiment of the Multi-Friction Sleeve Penetrometer.

| | Multi-Friction Sleeve Penetrometer | 15 cm² CPT Module |
|---|---|---|
| Total Length | 109 cm | 61 cm |
| Baseline diameter | 43.7 mm | 43.7 mm |
| Tip Resistance ($q_c$) | N/A | |
| Capacity | | 225 kN |
| Overload Capacity | | 150% |
| Accuracy | | 0.2% |
| Pore Pressure ($u_2$) | N/A | |
| Capacity | | 3.5 Mpa |
| Overload Capacity | | 150% |
| Accuracy | | 0.1% |
| Friction Sleeve ($f_s$) | | |
| Capacity | 45 kN | 45 kN |
| Load Cell | Full Bridge | Full Bridge |
| Overload Capacity | 150% | 150% |
| Precision | 44–89 N | 44–89 N |
| Hysterisis | 22 N | 22 N |
| Length | 11.00 cm | 16.39 cm |
| Surface Area | 151 cm² | 225 cm² |
| Surface Roughness ($R_a$) | 0.50–250 m | 0.50 m |
| Inclinometers | | |
| Range | | 20 |
| Accuracy | | 10% |

As seen in FIG. 3 and Table 2, individual, full bridge load cell sensors 12 were selected. Although, subtraction type load cells may be used, with a subtraction design, the fourth sleeve 4 friction would have been determined by subtracting the force acting on the lead module (being either an uninstrumented tip or a CPT module 22 (shown)), the first three attachment sleeves (1, 2, 3), and the exposed mandrel (5, 6, 7) between each consecutive sleeve. The load cell 12 consists of a thin cylinder instrumented on the inside with a full eight strain gauge bridge. The cylinder is separate from the load bearing center mandrel and is loaded in compression by the friction sleeve transferring the sleeve friction to the end of the cylinder. The individual load cell 12 capacities are 45 kN each with an overload tolerance of 150%. The load cells 12 are 11 cm in length, have 150 cm² surface area, and a surface roughness of 0.50–250 m.

Figure 4:
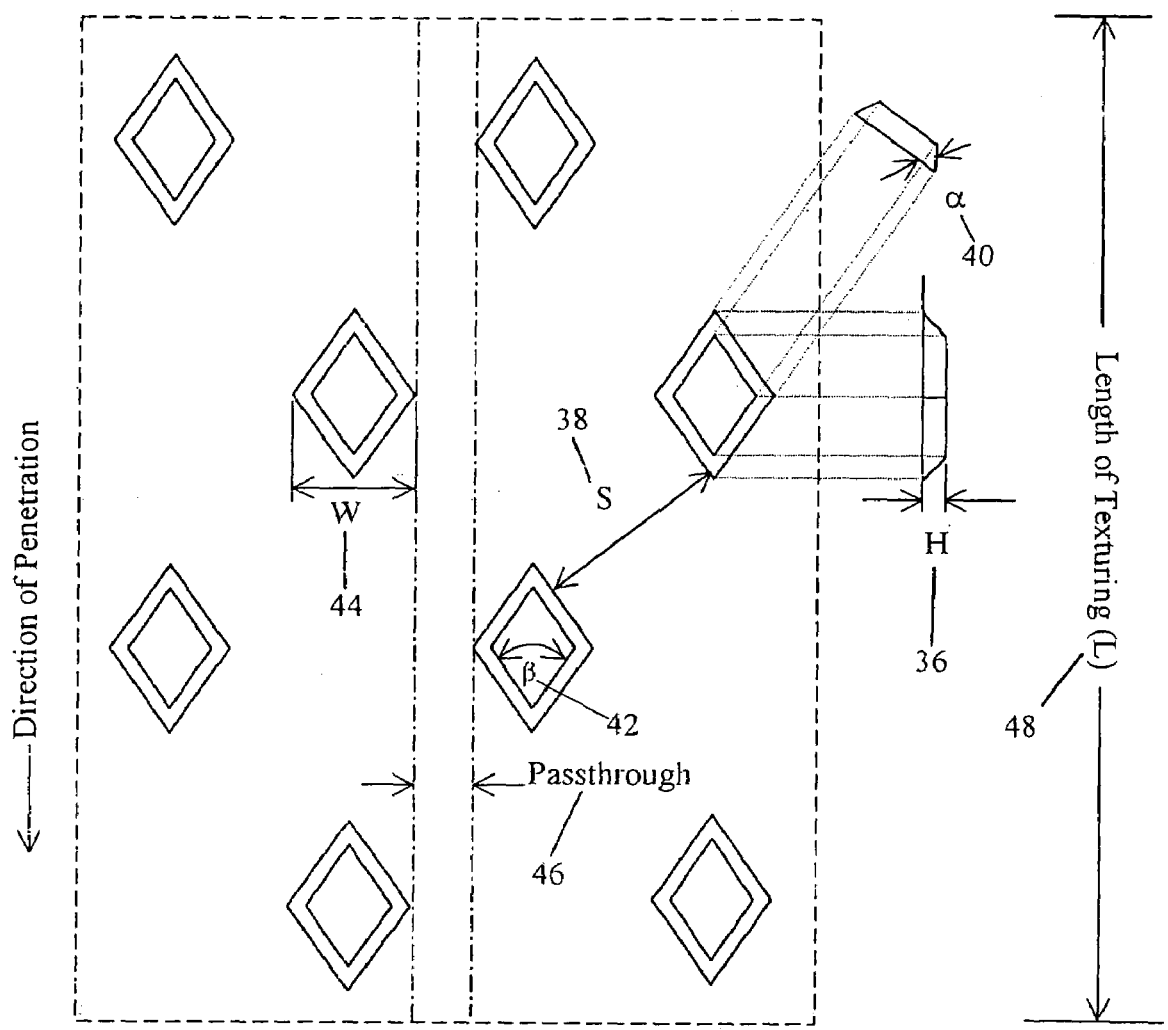
FIG. 4 is a schematic diagram showing a planar projection of a diamond textured sleeve design.

The individual friction sleeves 1–4 can be configured to be removable for ease of assembly and maintenance. The texture of the sleeves 1–4 is designed to be "self-cleaning" and thereby not result in soil particles clogging the texture and changing the surface roughness during a sounding. At the same time, the texture of the sleeves 1–4 is designed to induce internal shearing of the soil, rather than only sliding of soil particles along the interface at high roughness. The percentage passthrough 46 for the textured sleeves 1–4 ranges from 0 to 46 percent. Furthermore, the surface designs are machineable into a wide range of surface roughness values ($R_a$=0.01–116 µm) for conventional geomaterials. Accordingly, the texturing patterns for the attachment module 10 are based on a staggered diamond configuration as shown in FIG. 4, with the corresponding surface roughness values for a number of different roughness parameters shown in Table 3 below. As evident, the average surface roughness ($R_a$) values for the diamond textured sleeves ranged from 0.05 to 250 μm, including the conventional smooth sleeve. Different staggered diamond patterns for the friction sleeves are achieved by varying aspects such as the height (H) 36 between approximately 0.0005 to 2.0 mm, the diagonal spacing (S) 38 between approximately 4.6 to 35.4 mm, and the penetration angle (β) 42 between approximately 5 to 120 degrees. The width (W) 44 and angle (α) 40 remained constant at 5.3 mm and 45 degrees respectively, and the percent passthrough ranges from approximately 0–77%. Each sleeve 1–4 is machined so that the base diameter equals the diameter of a conventional smooth sleeve (44.09±0.05 mm) and so that the diamond pattern extends beyond that surface.

TABLE 3

Summary of Diamond Texturing Pattern Dimensions.

| Diamond Dimension | Range Investigated | Reference Configuration |
| --- | --- | --- |
| Height (H) | 0.0005–2.0 mm | 1.0 mm |
| Penetration Angle ( ) | 15°–120° | 60° |
| Diagonal Spacing (S) | 4.6–12.5 mm | 6.3 mm |
| [Percent Passthrough] | [0–46%] | [16%] |
| Diamond Width (W) | 5.3 mm | 5.3 mm |
| Diamond Angle ( ) | 45° | 45° |
| Average Roughness ($R_a$) | 0.5–250 m | 185 m |

Figure 5A:
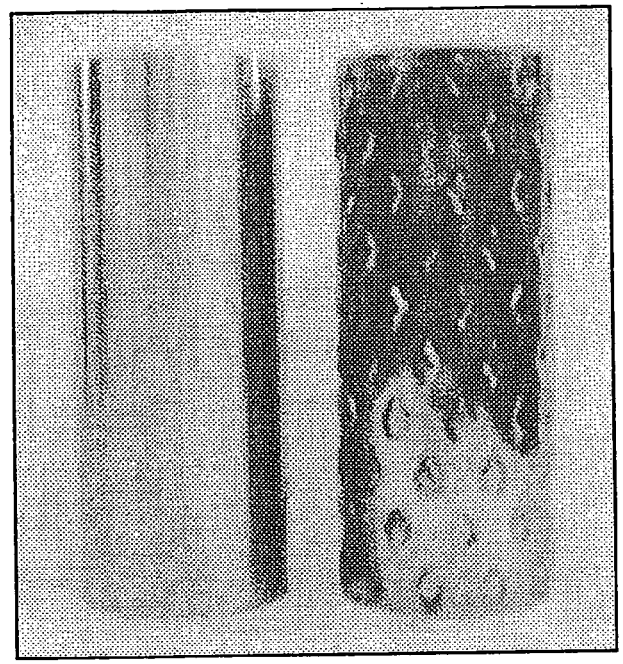
FIGS. 5A and 5B are pictorial representations of embodiments of sleeves, showing (a) smooth and diamond textured sleeves, (b) increasing roughness, (c) decreasing spacing and (d) increasing penetration angle.
Figure 5A:
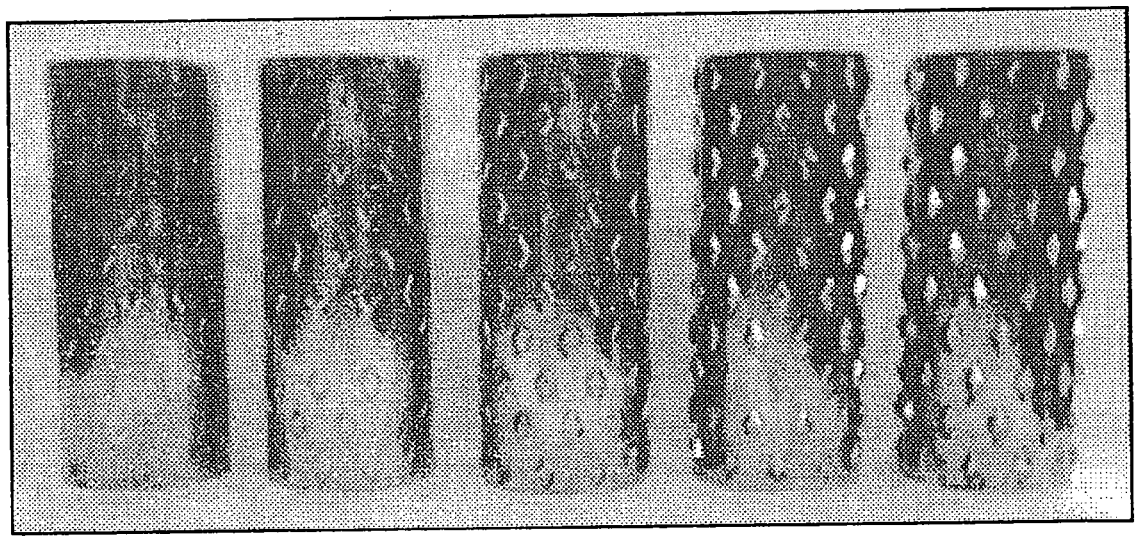
Figure 5B:
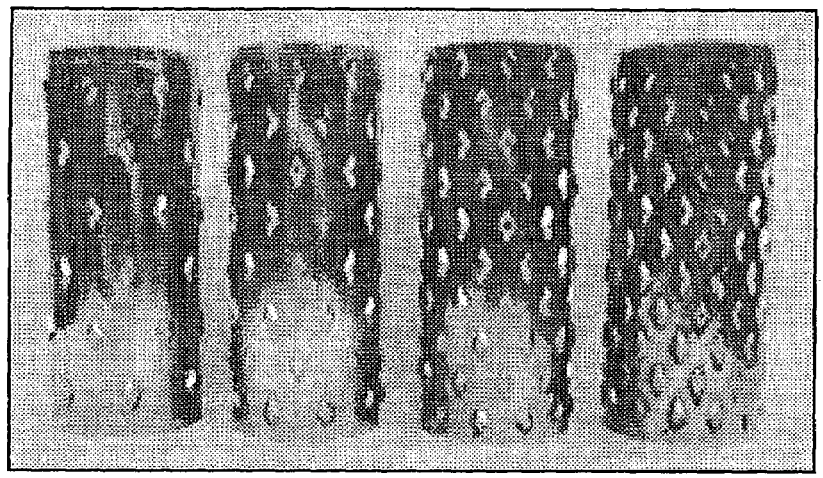
Figure 5B:
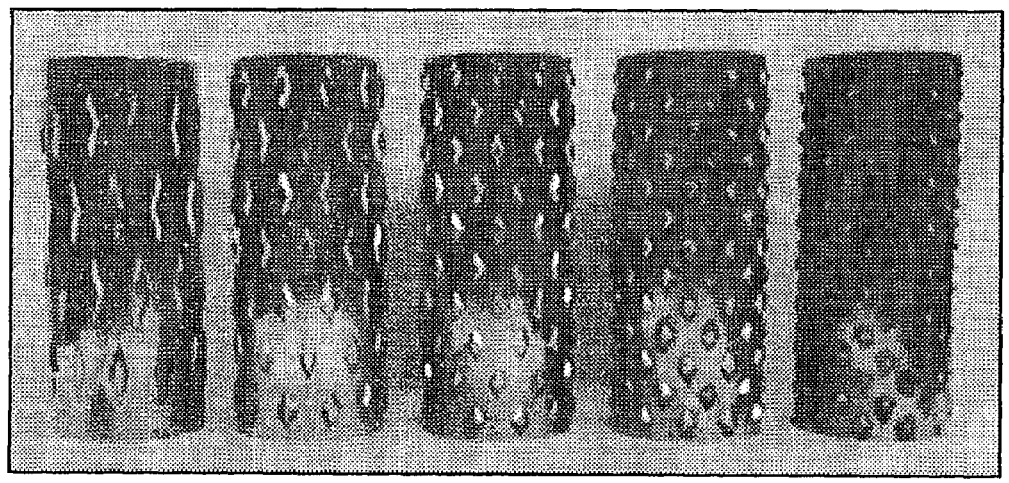

In excess of twenty different diamond surface textured friction sleeves in addition to the conventional smooth sleeve have been manufactured and tested for application with the attachment module. The textured sleeves were specifically designed to investigate the effect of diamond height (H) 36, diagonal spacing (S) 38, penetration angle (β) 42, and length of texturing (L) 48 on the friction sleeve measurement. FIGS. 5A and 5B show friction sleeves, including (a) illustrating a conventional smooth sleeve and a diamond surface textured sleeve; (b) showing sleeves of increasing roughness; (c) showing sleeves of decreasing spacing 38; and (d) showing sleeves with increasing penetration angle 42.

Due to the bilinear relationship of surface roughness to interface strength, small changes in roughness have a negligible effect on the interface strength so long as surface roughness is in the stable upper portion of the curve (see FIG. 1). In the present embodiment having diamond patterned sleeves 1–4, the pattern design is relatively resistant to wear since the individual asperities, or diamonds, have a large projected cross-sectional area. Nonetheless, it is recommended that all sleeves be machined out of a pre-hardened metal alloy with a Rockwell C hardness of about 30. Such hardness, as was used for the diamond patterned sleeves, will minimize wear and extend the service life while maintaining relative ease in machining. Accordingly, it is anticipated that minor changes due to wear in surface roughness on most diamond textured sleeves should have a negligible effect on the measured sleeve friction.

Since it is evident that a shorter sleeve 1–4 provides increased sensitivity to soil classification and stratigraphic features, including distinct interfaces and thin soil layers, the present embodiment utilizes a sleeve having a shorter length of only 11 cm, as opposed to aA more typical length of 16.39 cm. In addition, the sleeves 1–4 are positioned well behind the penetrometer tip, thus negating the requirement that the CPT sleeve length 30 be about 3 to 5 times the module diameter 35 (ASTM D5778 1995) (see FIG. 3). As the sleeve friction was found to vary near the tip as a result of the highly sheared zone that developed around the tip during penetration, a standard sleeve length to diameter ratio was established in an attempt to normalize this effect between different size penetrometers (i.e. 10 and 15 cm$^2$). In a preferred embodiment, the sleeves 1–4 are 11 cm long (surface area=151 cm$^2$), which results in a surface area similar to the standard 10 cm$^2$ sleeve (150 cm$^2$). The minimum length of the attachment sleeves 1–4 is determined by the need to ensure that an adequate surface area, necessary for the effect of the texture to be established, is possible and that a practical perspective, as far as dimensional constraints of the individual load cell system, is selected.

As shown in FIG. 3, the module attachment 10 is designed for ready assembly behind a conventional CPT module 22. In this configuration, conventional CPT $q_c$, $f_s$, and $u_2$ measurements are obtained in the same sounding and provide the opportunity to compare the module attachment 10 measurements with the standardized in situ measurements. This configuration enables rapid identification of the subsurface stratigraphy encountered in each sounding and separates the differences due to lateral variability from those due to changes in sleeve texture.

Since one objective of the multi-friction sleeve attachment module 10 is to obtain multiple measurements of interface strength under the same conditions and in the same sounding, all attachment sleeves 1–4 are optimally positioned beyond the influence of the high shear zone. To meet these requirements, a conventional 15 cm$^2$ CPT module 22 with an extended electronic housing 24, 26 enabled the lead edge of the first (lowest) attachment sleeve 1, $f_s$#1, to be located 61 cm (~14 diameters) behind the CPT tip 34. In embodiments where an uninstrumented tip may be used instead of a CPT tip 34, the positioning of the sleeves 1–4 beyond the influence of the high shear zone around the tip is still recommended.

The attachment module 10 is designed to permit efficient disassembly/reassembly between soundings and further permits modifications with only minimal adjustments. As shown in FIG. 3, the attachment module 10 is a jointed mandrel design whereby each individual load cell unit (mandrel 5–8, load cell 12, and sleeve 1–4) is comprised of separate components. With this modularity, the number of different custom components is minimized. Furthermore, modifications to individual load cells 12 can be performed with relative ease and a damaged load cell unit 12 can be easily replaced with a backup unit in the field. In addition, the number of individual load cells 12 can be increased or decreased freely since each load cell unit 12 is mechanically self contained and the data acquisition system 68 (see FIG. 6) can be configured for a range of different configurations with only minor adjustments.

In order to counteract any adverse affects on the measurement of the friction sleeves 1–4 behind the tip 34 due to inadequate module stiffness, the connections between the attachment module 10 and the CPT module 22 are of sufficient stiffness. In particular, the connections between the CPT 22 and attachment 10, and between each structural component of the attachment 10 are designed to withstand estimated lateral forces that could induce module bending under common testing configurations. The module stiffness between the CPT 22 and the attachment 10 is additionally increased by minimizing the inner diameter of the sleeve mandrels 16. This minimization is facilitated by the size of the cable required for down-hole digital processing is smaller than the cable required for conventional up-hole signal conditioning.

The attachment module is further configured for use below the water table and, therefore, a watertight seal should be maintained in the areas where electronics are present. The watertight seal is accomplished by sealing each joint with one or more O or X-rings.

Figure 6:
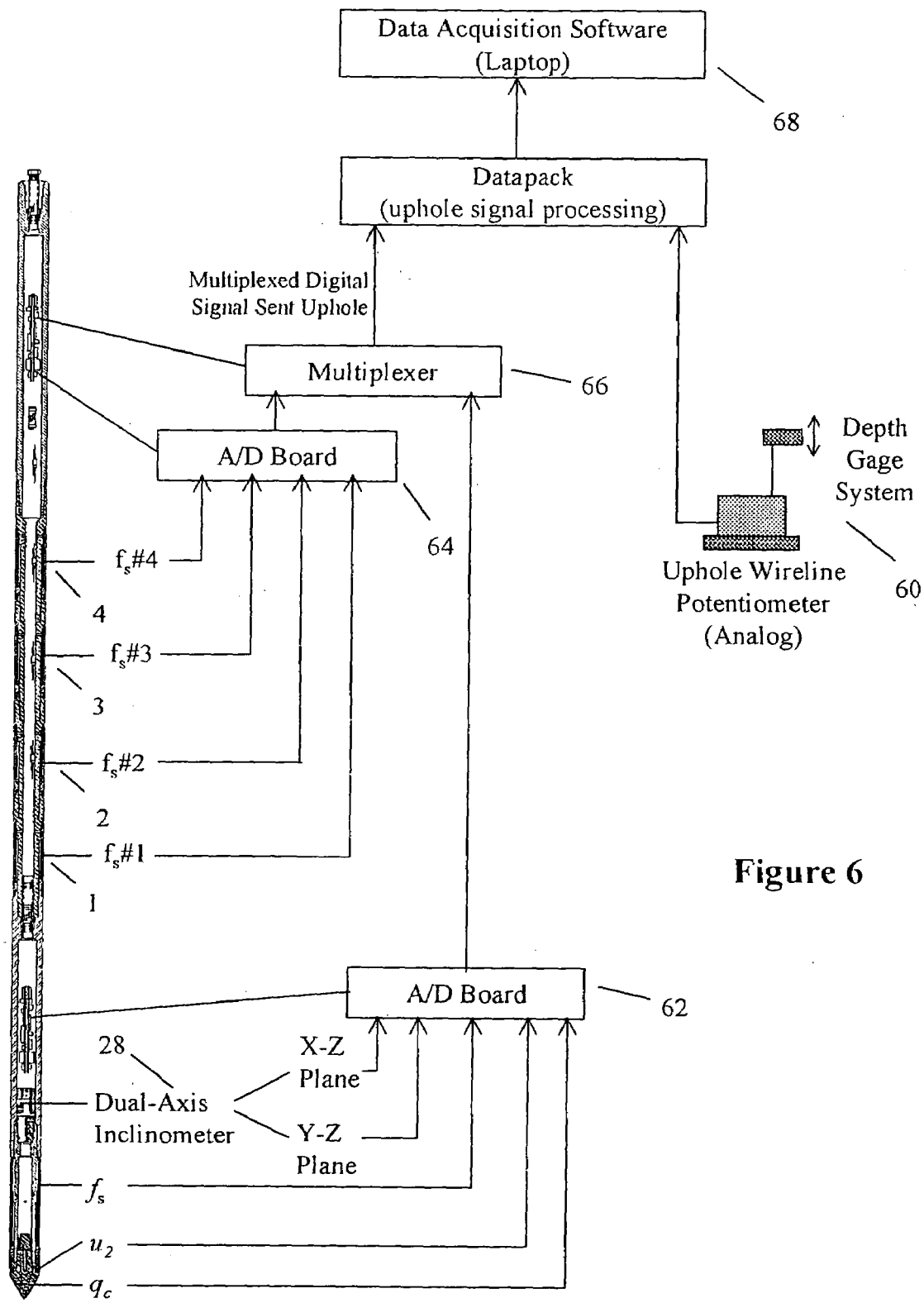
FIG. 6 is a schematic diagram of an embodiment of a data acquisition system for the combined CPT module-attachment module system.

The attachment module 10 is further configured with a data acquisition system that allows real-time review of data. FIG. 6 is a schematic of the data acquisition system used in conjunction with the attachment module 10 and with a conventional CPT 22. The hardware in the CPT module 22 is used to measure the $q_c$, $f_s$, and $u_2$ values and the hardware in the attachment module 10 is used to individually measure the force on each of the four sleeves 1–4 ($f_s\#1$, $f_s\#2$, $f_s\#3$, and $f_s\#4$) at each measurement increment. In addition, a dual axis inclinometer system 28 is incorporated in the CPT module 22 to enable continuous monitoring of verticality during penetration. Penetration depth is monitored up-hole using a wireline potentiometer 60. With nine individual measurements being obtained downhole by the complete CPT module 22 and attachment module 10 system, a downhole analog-to-digital signal conditioning system 62 is used. To maintain the independence of the CPT module 22, the CPT analog signals are conditioned and converted to digital signals separately within the CPT module 22 housing. The attachment module 10 signals are conditioned in a similar fashion in an A/D board 64 and then multiplexed 66 with the digital signals from the CPT module 22 and relayed up-hole to the data acquisition system 68.

When in use, a series of calibration tests should be performed to assess the performance of the multi-friction sleeve attachment system. First, prior to assembly of the attachment module 10, each load cell 12 should be individually calibrated, without signal conditioning against a NIST traceable load cell, by applying an excitation directly to the full bridge and monitoring the output during a load-unload cycle. Second, each attachment module 10 load cell 12 in the fully assembled CPT-attachment module should be calibrated by undergoing a load-unload cycle against a NIST traceable load cell. This calibration enables both the calibration of each load cell 12 through the signal conditioning system, as well as assessment of mechanical cross-talk between the multiple sleeve load cells.

In another embodiment, a method is provided for obtaining multiple sleeve friction measurements at each measurement depth within a single sounding and enhances the data obtained in conventional CPT soundings with measurements of sleeve friction for different sleeve surface roughnesses. In particular, the attachment module 10 system provides a method for obtaining seven simultaneous measurements at each measurement increment while monitoring module verticality, full analog-to-digital conversion and multiplexing of signals downhole, the arrangement of four individual sleeve load cell sensors in series, and the ability to rapidly exchange sleeves 1–4 between consecutive soundings. The diamond texturing pattern for sleeves is "self-cleaning" and, depending on the dimensions of the diamonds, induces shearing within the soil as opposed to at the interface, thus providing more accurate frictional measurements. The individual, modular load cell 12 design performs well and has a linear calibration range with minimal hysteresis and mechanical cross-talk between individual sleeve load cells 12.

Figure 7:
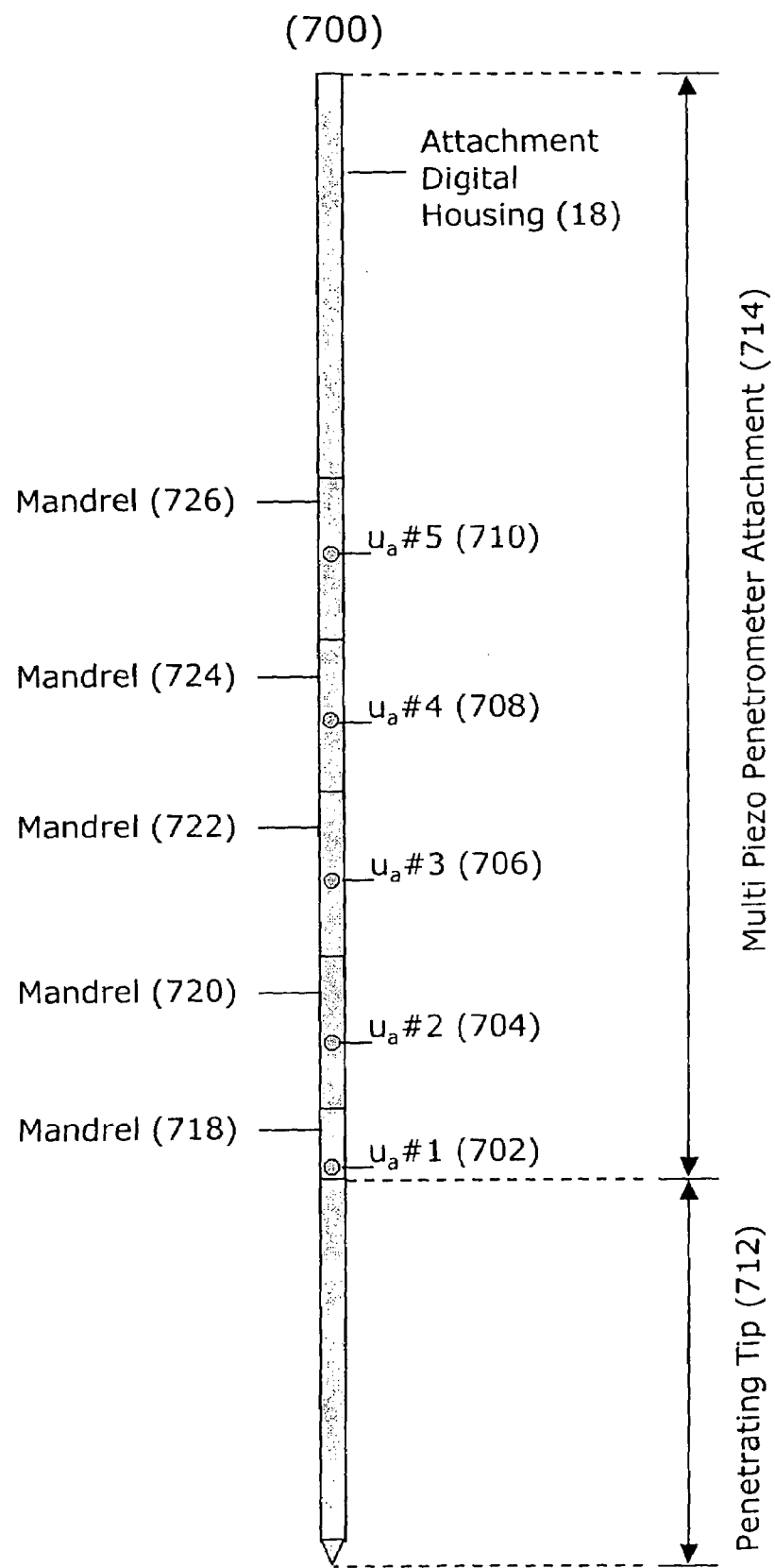
FIG. 7 is a schematic diagram of an embodiment of a multi-piezo penetrometer with an uninstrumented penetrating tip that measures the pore fluid pressure of the soil at a particular subsurface location.

FIG. 7 is a schematic diagram of an embodiment of a multi-piezo penetrometer with an uninstrumented penetrating tip that measures the pore fluid pressure of the soil at a particular subsurface location. The penetrometer 700 comprises an attachment module 714 that is coupled to the uninstrumented penetrating tip 712. The attachment module 714 includes a digital housing 18, a plurality of mandrels 718, 720, 722, 724, 726 and a plurality of individual piezo sensors 702, 704, 706, 708, 710. In general, a piezo sensor is any type of sensor that measures the pore fluid pressure by utilizing one of a number of techniques based on pneumatic, mechanical or hydraulic principles. The piezo sensors measure the pore fluid pressure generated by the penetrating tip 712 and any subsequent dissipation that occurs as a result of the relative spatial and temporal separation of the tip and the sensors.

The mandrels 718, 720, 722, 724, 726 are coupled together in series to one another. For example, referring to FIG. 7, mandrel 718 is coupled to mandrel 720, which in turn is connected to mandrel 722. At least one mandrel is coupled with at least one piezo sensor. Referring to FIG. 7, each mandrel is coupled with independent piezo sensors. Each individual piezo sensor obtains an in situ measurement of pore fluid pressure at each measurement depth that corresponds to the location of each mandrel on the attachment module. The individual piezo sensor has a value at each measurement depth in a single sounding, which the value corresponds to the individual in situ measurements of pore fluid pressure at the measurement depths. Each piezo sensor provides individual in situ measurement of pore fluid pressure at each measurement depth in a single sounding. Thus, the multi-piezo penetrometer 700 provides five individual in situ measurement of pore fluid pressure at each measurement depth of the piezo sensors in a single sounding.

Figure 8:
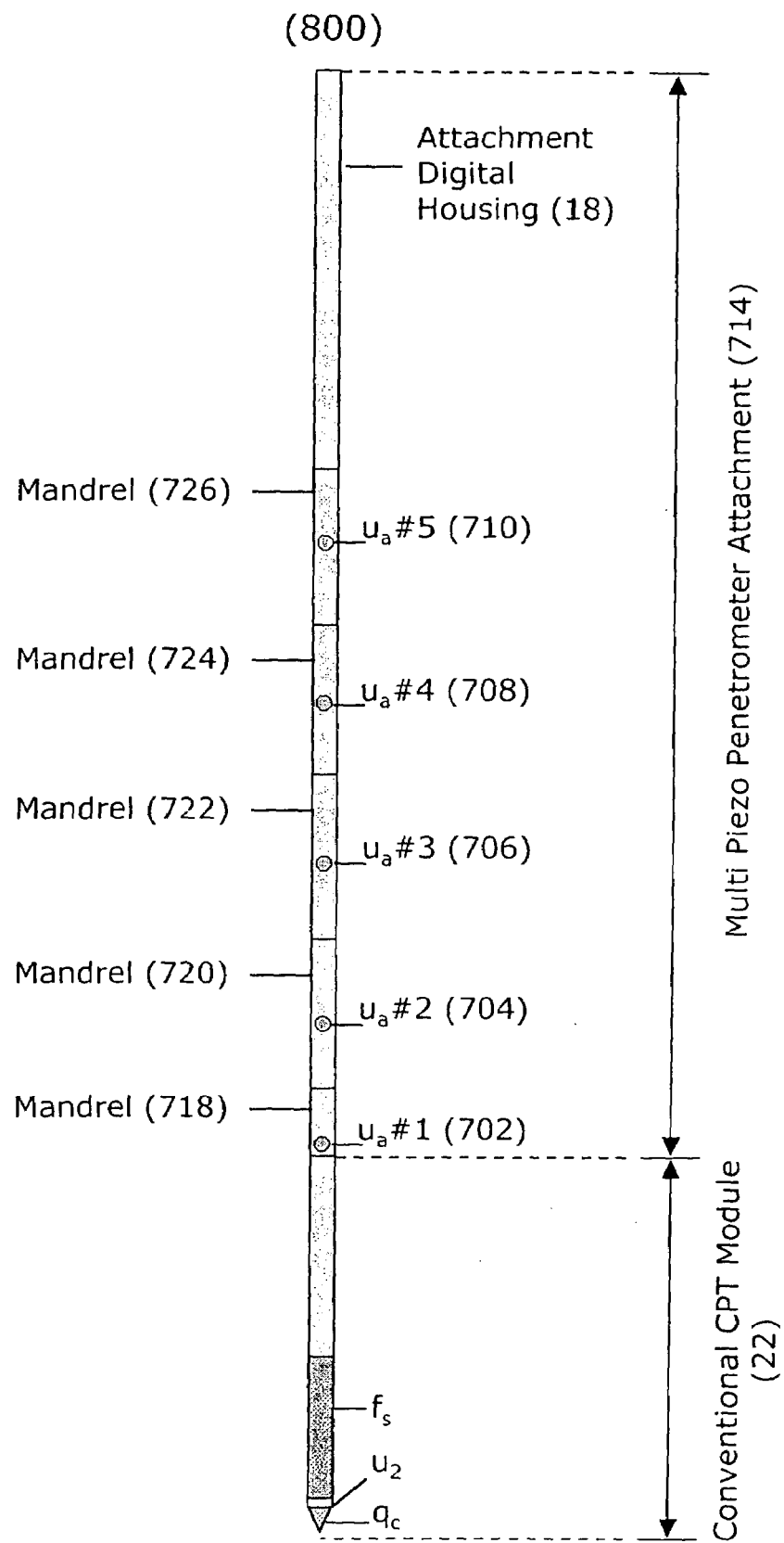
FIG. 8 is a schematic diagram of an embodiment of a multi-piezo penetrometer with an instrumented penetrating tip.

FIG. 8 is a schematic diagram of an embodiment of a multi-piezo penetrometer with an instrumented penetrating tip. The penetrometer 800 is similar to the penetrometer 700 and therefore includes multi-piezo attachment module 714, which includes a digital housing 18, a plurality of mandrels 718, 720, 722, 724, 726 and a plurality of piezo sensors 702, 704, 706, 708, 710. However, penetrometer 800 does not include an uninstrumented penetrating tip 712 as in penetrometer 700, as shown in FIG. 7. Instead, penetrometer 800 includes an instrumented penetrating tip, preferably a conventional CPT module 22.

Figure 9:
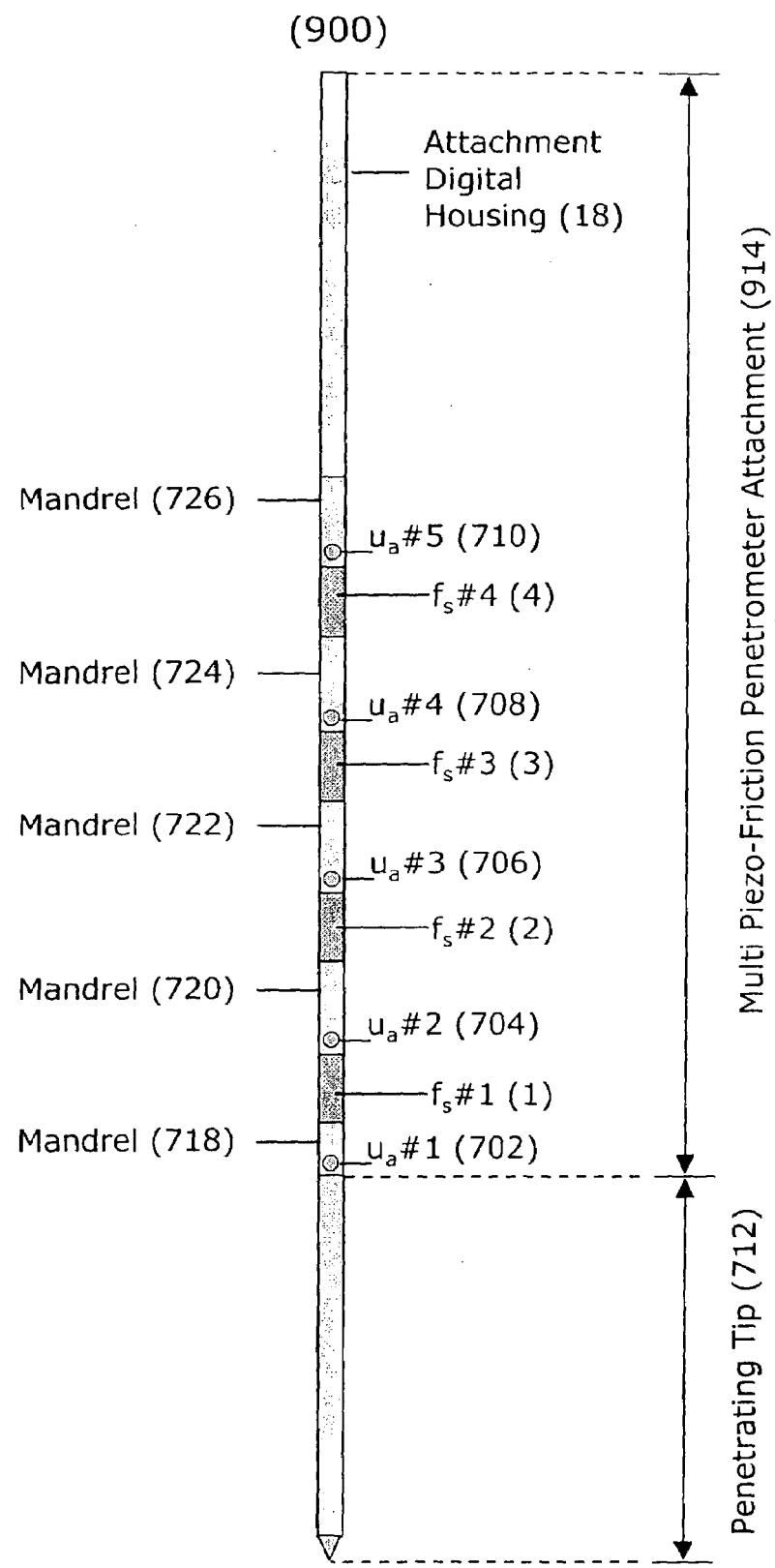
FIG. 9 is a schematic diagram of an embodiment of a multi-piezo-friction penetrometer with an uninstrumented penetrating tip and an attachment module that includes multiple load cells.

FIG. 9 is a schematic diagram of an embodiment of a multi-piezo-friction penetrometer with an uninstrumented penetrating tip and an attachment module that includes multiple load cells. The penetrometer 900 is similar to the penetrometer 700 and therefore includes penetrating tip 712 and an attachment module 914 that includes a digital housing 18, a plurality of mandrels 718, 720, 722, 724, 726 and a plurality of piezo sensors 702, 704, 706, 708, 710. In addition, however, the attachment module 914 further includes multiple load cells, which are attached to friction sleeves 1–4. Because module 914 includes both the friction sleeve 1–4 and piezo sensors 702, 704, 706, 708, 710, the module 914 can be referred to as multi-piezo-friction attachment module.

At least one piezo sensor is coupled adjacent to at least one load cell. For example, the mandrel 718 with the piezo sensor 702 is coupled adjacent to the load cell with the friction sleeve 1, which is also coupled adjacent to the mandrel 720 with the piezo sensor 704. The mandrel 720 is coupled adjacent to the load cell with the friction sleeve 2, which is also coupled adjacent to the mandrel 722 with the piezo sensor 706. The mandrel 722 is coupled adjacent to the load cell with the friction sleeve 3, which is also coupled adjacent to the mandrel 724 with the piezo sensor 708. The mandrel 724 is coupled adjacent to the load cell with the friction sleeve 4, which is also coupled adjacent to the mandrel 726 with the piezo sensor 710. Thus, the load cells and the mandrels are coupled in sequence, as shown in FIG. 9.

Each load cell has a friction sleeve with a surface texture of a particular smoothness and/or roughness. Each load cell individually measures the interface resistance due to the penetration of sleeves 1–4 with selected surface textures into the soil. The friction sleeve can induce internal shearing of the soil, which enables the piezo sensors 702, 704, 706, 708, 710 to measure the pore fluid pressure induced by each friction sleeve of the individual load cells at a particular subsurface location. For example, the piezo sensor 708 measures the pore fluid pressure induced by the friction sleeve 3. The piezo sensor has a value at a measurement depth for each friction sleeve of the individual load cells in a single sounding, which the value corresponds to the individual in situ measurements of pore fluid pressure at the measurement depth for each load cell. The piezo sensor is isolated to measure the pore fluid pressure generated for each load cell at a particular subsurface.

Figure 10:
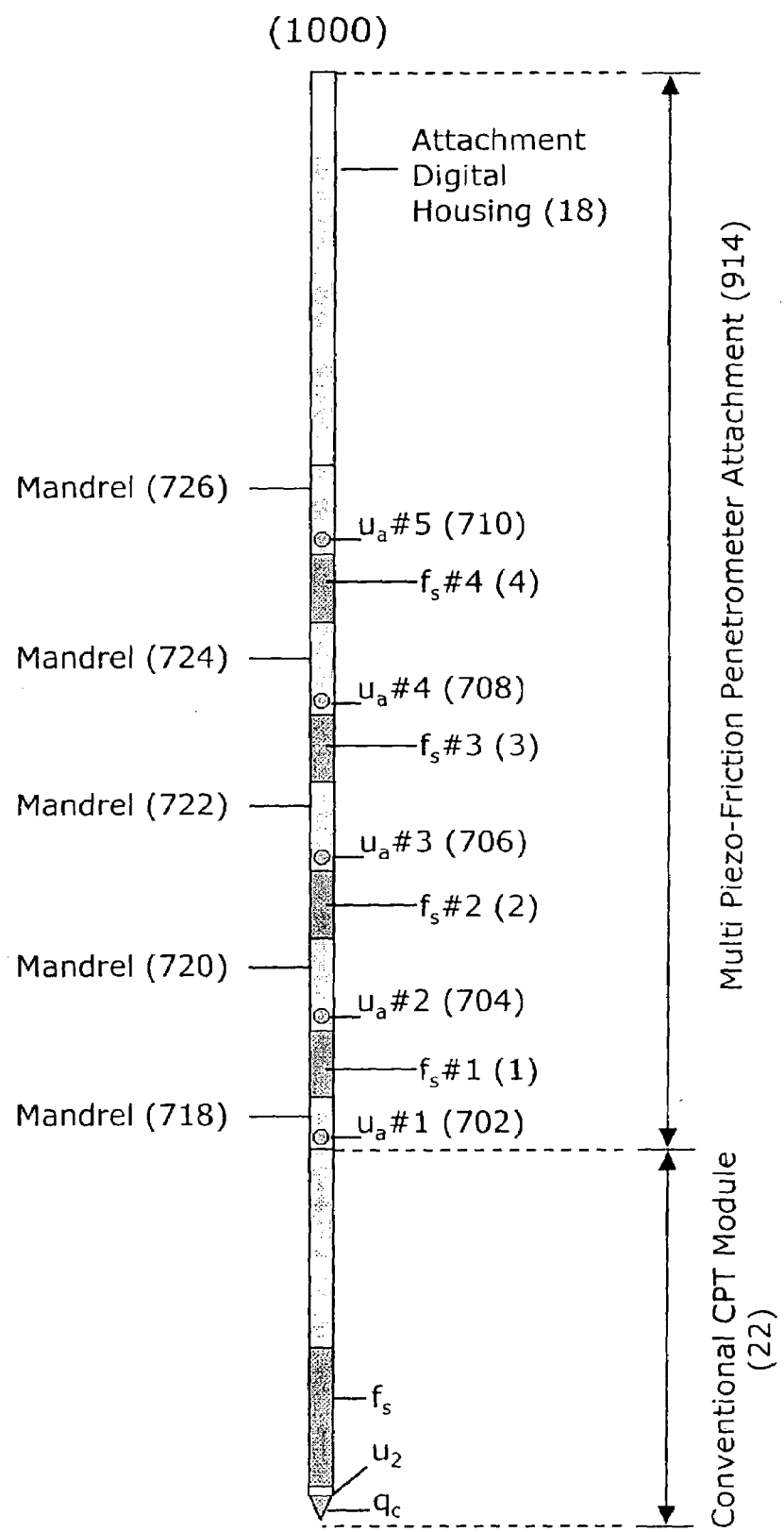
FIG. 10 is a schematic diagram of an embodiment of a multi-piezo-friction penetrometer with an instrumented penetrating tip and an attachment module that includes multiple load cells.

FIG. 10 is a schematic diagram of an embodiment of a multi-piezo-friction penetrometer with an instrumented penetrating tip and an attachment module that includes multiple load cells. The penetrometer 1000 is similar to the penetrometer 900 and therefore includes a multi-piezo-friction attachment module 914 that includes a digital housing 18, a plurality of mandrels 718, 720, 722, 724, 726, a plurality of piezo sensors 702, 704, 706, 708, 710 and multiple load cells that are attached to friction sleeves 1–4. However, penetrometer 1000 does not include an uninstrumented penetrating tip 712 as in penetrometer 900, as shown in FIG. 9. Instead, penetrometer 1000 includes an instrumented tip, preferably a conventional CPT module 22.

Figure 11:
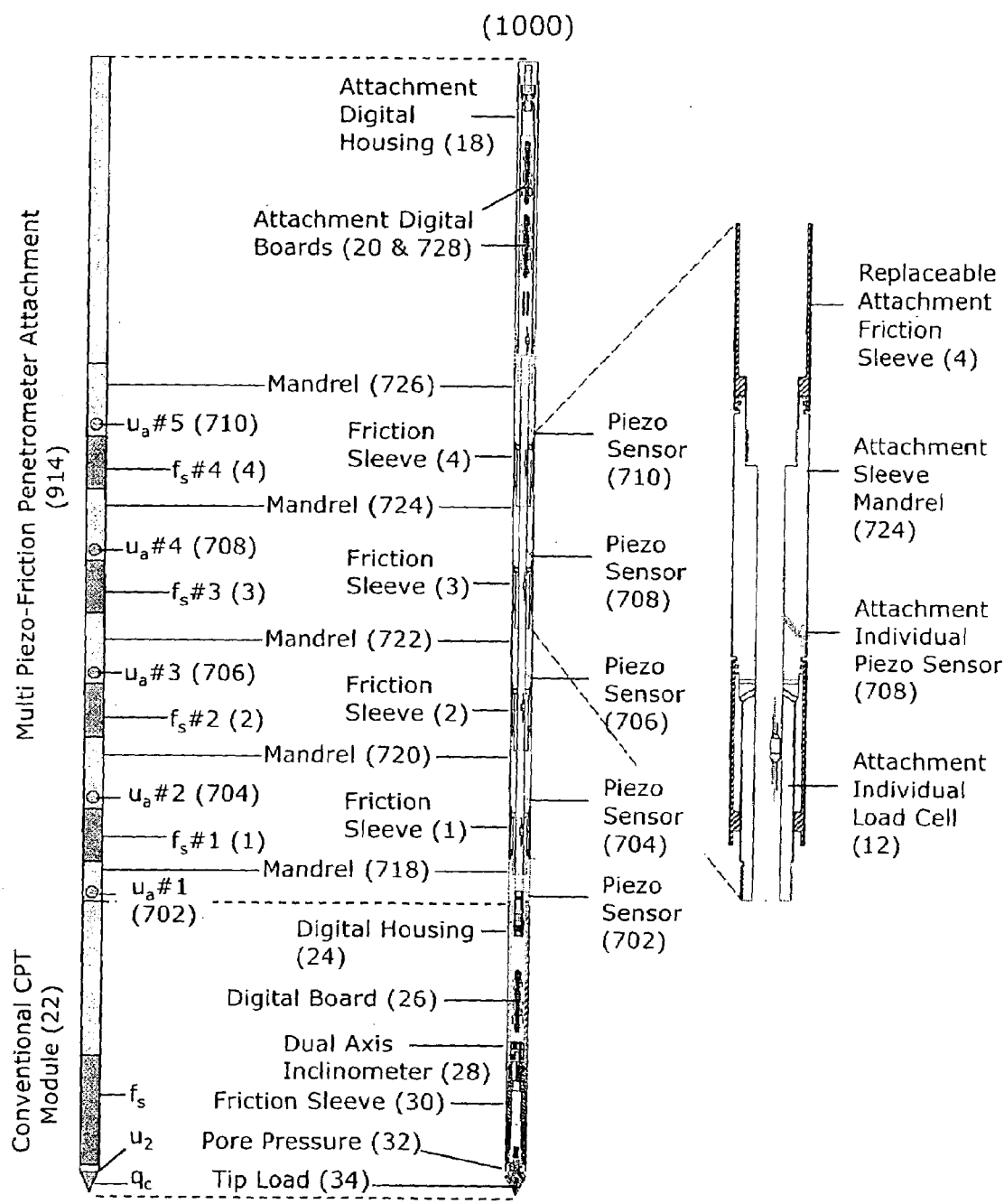
FIG. 11 is a schematic diagram illustrating design detail (b) and a partial exploded view (c) of an embodiment of a multi-piezo-friction penetrometer.

FIG. 11 illustrates the schematic diagram (a) of penetrometer 1000, which is the same diagram shown in FIG. 10. FIG. 11 further illustrates a design detail (b) of penetrometer 1000 with the conventional CPT module 22 and the attachment module 914 that includes load cells with friction sleeves 1–4 coupled adjacent to mandrels 718, 720, 722, 724, 726 with piezo sensors 702, 704, 706, 708, 710. FIG. 11 further illustrates a partial exploded view (c) of the penetrometer 1000, which shows the piezo sensor 708 that is integrated into the mandrel 724.

Figure 12:
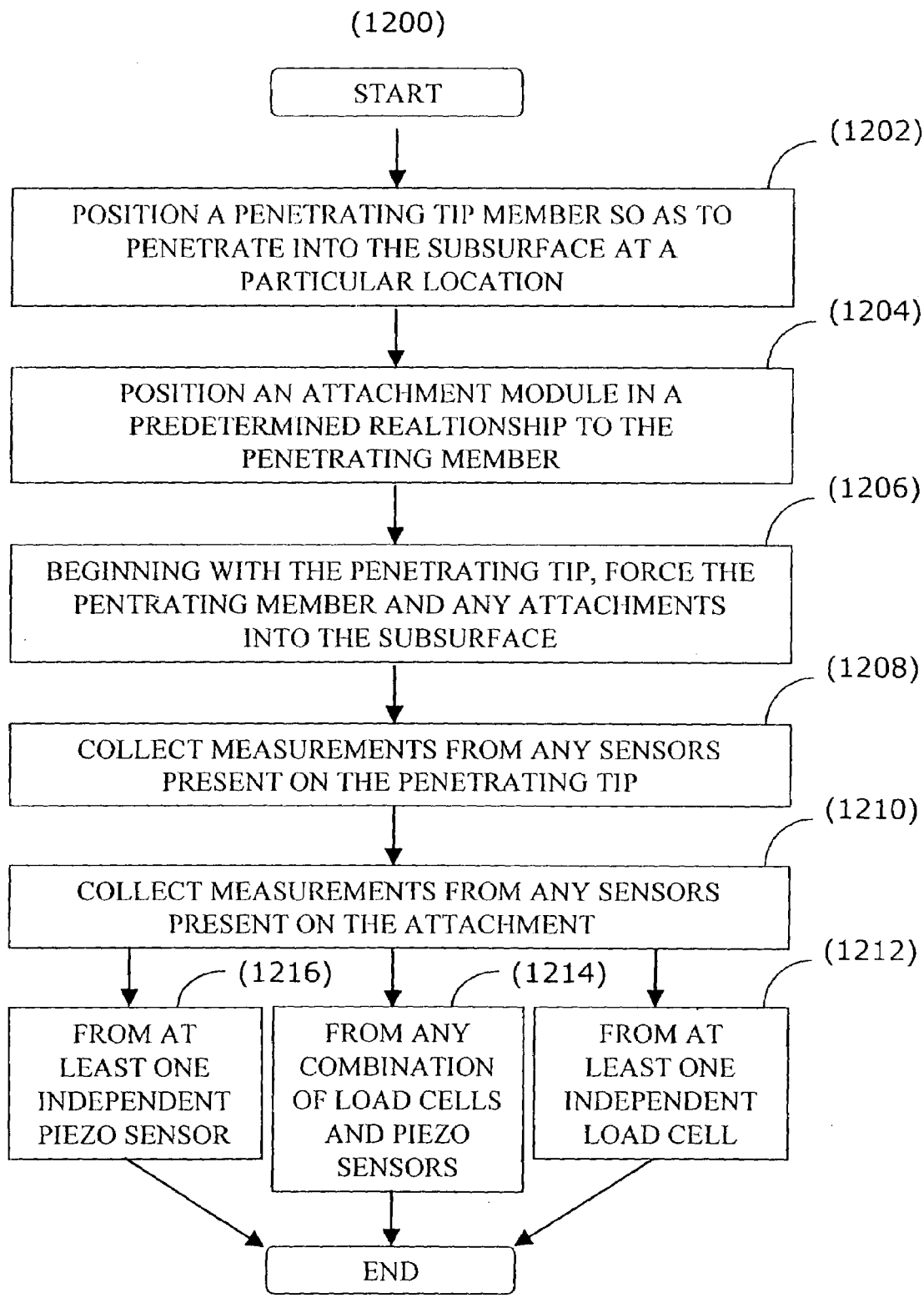
FIG. 12 is a flow diagram that illustrates an embodiment of operation for determining in situ pore fluid and soil properties.

FIG. 12 is a flow diagram that illustrates an embodiment of operation for determining in situ pore fluid and soil properties with the various multi-sensor systems described herein. In block 1202, the operation 1200 comprises positioning a penetrating tip member so as to penetrate into soil at a particular subsurface area. An attachment module is positioned in a predetermined relationship to the penetrating tip member so as to form a penetrometer comprised of at least the penetrating tip member and the attachment module, as shown in block 1204. The penetrometer is forced into the soil beginning with the penetrating tip member, as shown in block 1206, and the measurements are collected from the penetrating tip member (e.g., convention CPT module 22), as shown in block 1208.

It should be noted that the penetrometers 700, 800, 900, 1000 measure pore fluid pressure measurements and transmit the measurement data to a data acquisition system. The data acquisition system obtains the pore fluid pressure values at each measurement increment on each piezo sensor located in the mandrel, which enables the data acquisition system to provide contemporaneous review of pore fluid pressure data. The measurement data is converted to digital signals, multiplexed, and then relayed to the data acquisition system.

Measurements from the attachment module are collected as shown in block 1210. The attachment module can include at least one piezo sensor or at least one load cell or both. The attachment module can comprise at least one independent load cell and not the piezo sensor. Each of the load cells is comprised of a corresponding plurality of friction sleeves that obtains an in situ measurement of interface strength at each measurement depth that corresponds to the location of the load cell on the attachment module, as shown in block 1212. The attachment module can comprise at least one mandrel and not the load cells, wherein at least one mandrel comprises at a piezo sensor that obtains an in situ measurement of pore fluid pressure at each measurement depth that corresponds to the location of each mandrel on the attachment module, as shown in block 1216. The attachment module can comprise any combination of independent piezo sensors and load cells that obtain in situ measurements of pore fluid pressure and interface strength, respectively, at depths that correspond to the locations of each sensor, as shown in block 1214. The piezo sensor is isolated to enable the measurement of the pore fluid pressure generated for each load cell. More particularly, the friction sleeve of each load cell can induce an internal shearing of the soil which enables the piezo sensor to measure the pore fluid pressure induced by each friction sleeve of the individual load cells at a particular subsurface.

It should be emphasized that the above-described embodiments of the present apparatus and methods, particularly, any "preferred" embodiments, are merely possible examples of implementations, merely set forth for a clear understanding of the principles of the apparatus and methods for determining pore fluid and soil response. Many variations and modifications may be made to the above-described embodiment(s) without departing substantially from principles thereof. All such modifications and variations are intended to be included herein and are protected by the following claims.

Therefore, having thus described the invention, at least the following is claimed:

1. An apparatus for determining in situ pore fluid and soil properties, the apparatus comprising:

a penetrating tip member configured to penetrate the soil; and an attachment module coupled to the penetrating tip member, the attachment module including at least one mandrel, each mandrel including at least one piezo sensor and a friction sleeve, wherein each piezo sensor is capable of obtaining an in situ measurement of pore pressure at a location corresponding proximal to the at least one mandrel on the attachment module, each friction sleeve of the respective mandrel having surface texture of a particular roughness that is capable of inducing an internal shearing of the soil, each piezo sensor of the respective mandrel being capable of measuring in situ pore fluid pressure from the induced shearing of the soil generated by the friction sleeve of the respective mandrel, wherein the attachment module further comprises at least one load cell, the load cell being coupled in sequence to the mandrel, wherein the at least one load cell obtains an in situ measurement of interface strength at a depth that is proximal to the location of the at least one load cell.

2. The apparatus of claim 1, wherein the attachment module further comprises a hollow inner chamber for containing data and power components.

3. The apparatus of claim 1, wherein the penetrating tip member further comprises a conventional cone penetration testing (CPT) module.

4. The apparatus of claim 3, further comprising a data acquisition system, the data acquisition system comprises:
   means for measuring penetration depth of the penetrating tip member and the attachment module;
   means for obtaining penetrating tip member measurement values;
   means for measuring verticality of the penetrating tip member; and
   means for obtaining pore fluid pressure values at each measurement increment on each piezo sensor located in the mandrel; end
   wherein the data acquisition system enables contemporaneous review of pore fluid pressure data.

5. The apparatus of claim 4, wherein the measurement data from each of the means for measuring is converted to digital signals, multiplexed, and then relayed to the data acquisition system.

6. The apparatus of claim 1, wherein the at least one piezo sensor is coupled adjacent to at least one load cell, the at least one piezo sensor being isolated to measure the pore fluid pressure generated for the at least one load cell, wherein a friction sleeve associated with the at least one load cell induces an internal shearing of the soil which enables the piezo sensor to measure pore fluid pressure.

7. The apparatus of claim 1, wherein each load cell further comprises a friction sleeve configured with a surface texture, where the surface texture has a corresponding surface roughness value;
   wherein each surface texture for a selected friction sleeve is configured to induce internal shearing of the soil as the attachment module penetrates the soil and to be self-cleaning, such that soil particles do not adhere to a surface of the friction sleeve.

8. The apparatus of claim 7, wherein the attachment module comprises multiple load cells, each load cell having a friction sleeve, the attachment module further comprising a vertical arrangement of the friction sleeves in ascending order according to increasing roughness of the surface texture, such that the least rough friction sleeve is placed closest to the penetrating tip member and the roughest friction sleeve is placed furthest away from the penetrating tip member.

9. The apparatus of claim 7, wherein the friction sleeve of each load cell has an average surface roughness of approximately 0.05 to approximately 250 μm.

10. The apparatus of claim 7, wherein each friction sleeve comprises a surface texture that is characterized by geometric parameters, including height, diagonal spacing, penetration angle, and width.

11. The apparatus of claim 10, wherein the geometric parameters of each of the surface textures comprise height variations from approximately 0.25 mm to approximately 2.0 mm, diagonal spacing from approximately 4.6 mm to approximately 12.5 mm, and penetration angles from approximately 30 degrees to approximately 120 degrees.

12. The apparatus of claim 1, wherein the at least one piezo sensor produces a signal at a corresponding depth in a single sounding, and the signals correspond to individual in situ measurements of pore fluid pressure at the corresponding depth.

13. The apparatus of claim 1, wherein pore fluid pressure measurements from the attachment module are transmitted to a data acquisition system.

14. A method of determining in situ pore fluid and soil properties, the method comprising the steps of:
   positioning a penetrating tip member so as to penetrate into the soil at a particular subsurface area;
   positioning an attachment module in a predetermined relationship to the penetrating tip member to form a penetrometer;
   forcing the penetrometer into the soil beginning with the penetrating tip member; and
   collecting attachment module measurements from at least one piezo sensor coupled to at least one mandrel, wherein the piezo sensor obtains an in situ measurement of pore fluid pressure at a depth that corresponds to the location of the at least one mandrel, wherein collecting attachment module measurements from a plurality of load cells comprises providing each of the load cells a corresponding plurality of mandrels and friction sleeves, the plurality of friction sleeves being configured to be removable, such that the arrangement of the friction sleeves along the attachment module portion of the penetrometer may be reconfigured into different order arrangements for measuring corresponding interface resistances of the friction sleeves.

15. The method of claim 14, wherein collecting attachment module measurements is performed by at least one individual load cell, the load cell including a friction sleeve that measures an interface resistance, the interface resistance corresponding to interface strength.

16. The method of claim 15, wherein collecting attachment module measurements from a plurality of load cells comprises each individual load cell with a friction sleeve configured with a surface texture, the surface texture of select friction sleeves being configured with a diamond-shaped pattern so as to induce internal shearing of the soil around the penetrometer as the penetrometer is penetrated into the soil.

17. The method of claim 15, wherein collecting attachment module measurements from a plurality of individual load cells comprises arranging a plurality of friction sleeves, wherein the friction sleeves are arranged in ascending order of vertically according to increasing roughness of the surface texture, such that the least rough friction sleeve is placed closest to the penetrating tip member and the roughest friction sleeve is placed furthest away from the penetrating tip member.

18. The method of claim 15, further comprising isolating the piezo sensor to measure the pore fluid pressure generated for each load cell, wherein the friction sleeve of each load cell induces an internal shearing of the soil, wherein the piezo sensor measures the pore fluid pressure induced by each friction sleeve of the individual load cells at a particular subsurface.

19. The method of claim 14, further including the steps of:
   measuring penetration depth of the penetrometer;
   measuring penetration tip member values;
   measuring verticality of the penetrating tip member, where the penetration depth, penetration tip member values, and verticality measurements comprise the drive tip measurements; and
   measuring pore fluid pressure at each measurement increment on each piezo sensors located in the mandrel.

20. The method of claim 19, further comprising converting analog measurement data from each of the measurements to digital signals, multiplexing, and then relaying the multiplexed data to the data acquisition system.

21. The method of claim 14, further comprising collecting penetrating tip measurements.

22. An apparatus for determining in situ pore fluid and soil properties, the apparatus comprising:
- a penetrating tip member configured to penetrate the soil; and
- an attachment module coupled to the penetrating tip member, the attachment module including at least one mandrel, each mandrel including at least one piezo sensor and a friction sleeve,
- each friction sleeve of the respective mandrel having surface texture of a particular roughness that is capable of inducing an internal shearing of the soil, each piezo sensor of the respective mandrel being capable of measuring in situ pore fluid pressure from the induced shearing of the soil generated by the friction sleeve of the respective mandrel,
- wherein the attachment module includes multiple mandrels, each mandrel having at least one piezo sensor and a friction sleeve configured with a surface texture, the attachment module further comprising a vertical arrangement of the friction sleeves.

23. The apparatus of claim 22, wherein the at least one mandrel comprises a leading mandrel and a trailing mandrel, a leading piezo sensor of the leading mandrel being capable of measuring the pore fluid pressure generated from a leading friction sleeve of the leading mandrel and the penetrating tip member,
- wherein a trailing piezo sensor of the trailing mandrel measures the pore fluid pressure generated from a trailing friction sleeve of the trailing mandrel, the leading friction sleeve and The penetrating tip member.

24. The apparatus of claim 23, wherein the measurement of the pore fluid pressure generated from the trailing friction sleeve is calculated by subtracting the measurements of the leading piezo sensor from the trailing piezo sensor.

* * * * *

UNITED STATES PATENT AND TRADEMARK OFFICE
CERTIFICATE OF CORRECTION

PATENT NO. : 7,201,060 B2 Page 1 of 1
APPLICATION NO. : 10/693624
DATED : April 10, 2007
INVENTOR(S) : Frost et al.

It is certified that error appears in the above-identified patent and that said Letters Patent is hereby corrected as shown below:

Column 17, Line 14

Delete the word "end" and replace with --and--

Signed and Sealed this

Thirty-first Day of July, 2007

JON W. DUDAS
*Director of the United States Patent and Trademark Office*